(12) United States Patent
Maher et al.

(10) Patent No.: US 6,186,665 B1
(45) Date of Patent: Feb. 13, 2001

(54) MOTOR ROTOR BEARING ASSEMBLY FOR A BLOOD PUMP

(75) Inventors: Timothy R. Maher, Orangevale; Pieter W. C. J. le Blanc, Citrus Heights; Tracy V. Petersen, Granite Bay; Kenneth C. Butler, Carmichael, all of CA (US)

(73) Assignee: Nimbus, Inc., Rancho Cordova, CA (US)

( * ) Notice: Under 35 U.S.C. 154(b), the term of this patent shall be extended for 0 days.

(21) Appl. No.: 09/237,721

(22) Filed: Jan. 26, 1999

(51) Int. Cl.[7] ..................................... F16C 23/04
(52) U.S. Cl. .................. 384/206; 417/356; 417/423.12
(58) Field of Search .................. 384/206, 208, 384/245; 417/356, 423.12

(56) References Cited

U.S. PATENT DOCUMENTS

| | | | |
|---|---|---|---|
| 4,994,078 | 2/1991 | Jarvik | 623/3 |
| 5,112,200 | 5/1992 | Isaacson et al. | 417/356 |
| 5,211,546 | 5/1993 | Isaacson et al. | 417/356 |
| 5,344,443 | 9/1994 | Palma et al. | |
| 5,527,159 | 6/1996 | Bozeman, Jr. et al. | 417/45 |
| 5,588,812 | 12/1996 | Taylor et al. | |
| 5,707,218 | 1/1998 | Maher et al. | 417/356 |
| 5,746,575 | 5/1998 | Westphal et al. | |
| 5,890,883 | 4/1999 | Golding et al. | 417/423.12 |

FOREIGN PATENT DOCUMENTS

| | | |
|---|---|---|
| WO 97/37698 | 10/1997 | (WO) . |
| WO 98/25657 | 6/1998 | (WO) . |
| WO 98/50089 | 11/1998 | (WO) . |

*Primary Examiner*—Lenard A. Footland
(74) *Attorney, Agent, or Firm*—Fish & Richardson P.C., P.A.

(57) ABSTRACT

A motor rotor assembly for use in a blood pump can include a motor rotor disposed within a blood flow conduit, an inflow bearing having an inflow ball-and-cup bearing interface disposed within the blood flow conduit proximal to an inflow port of the blood flow conduit, and an outflow bearing having an outflow ball-and-cup bearing interface disposed within the blood flow conduit proximal to an outflow port of the blood flow conduit. The motor can be rotatably mounted between the inflow bearing and the outflow bearing and an outer diameter of the outflow ball-and-cup bearing interface can be larger than an outer diameter of the inflow ball-and-cup bearing interface. A motor rotor assembly for use in a blood pump incorporating aspects of the invention may improve performance, reliability and longevity of the pump. A blood pump incorporating a motor rotor can further include a motor stator. These rotors and pumps can be used in both implantable and extracorporeal blood pumps.

36 Claims, 3 Drawing Sheets

MOTOR ROTOR BEARING ASSEMBLY FOR A BLOOD PUMP

STATEMENT AS TO FEDERALLY SPONSORED RESEARCH

The U.S. Government has a paid-up license in this invention and the right in limited circumstances to require the patent owner to license others on reasonable terms as provided for by the terms of NO1-HV58155 awarded by the National Heart, Lung, and Blood Institute.

TECHNICAL FIELD

The present invention relates to bearing assemblies and, more particularly, to bearing assemblies for securing a motor rotor useful in a rotary blood pump.

BACKGROUND

A number of rotary blood pumps presently are under development for application as either artificial hearts or cardiac assist devices. An axial flow blood pump, for example, typically includes a pump housing that defines a blood flow channel, an impeller mechanism mounted within the blood flow channel, an electric motor rotor coupled to actuate the impeller mechanism for blood pumping action, and an electric motor stator for actuating the rotor by electromagnetic force. The impeller mechanism may take the form of blades that are mechanically coupled to the rotor via a transmission shaft. Alternatively, the impeller blades can be mounted directly on the rotor. In this case, the rotor may form an elongated member that extends axially along the blood flow path. The impeller blades may be mounted about the rotor, for example, in a spiral-like pattern. The rotor is mounted in a bearing assembly.

Performance, reliability and longevity are critical performance factors for blood pumps due to their use as artificial hearts and/or cardiac assist devices. Among the most critical components of the pump is the motor. When the motor fails, the pump fails, leaving the residual function of the heart as the only means for continued cardiac operation and survival. Motor performance is highly dependent on the operation of the motor rotor and bearing assembly. The bearing assembly can be susceptible to seizure due to thrombosis at the bearing interface that restricts rotor movement. Excessive heat and/or inadequate heat removal near the bearing assembly can also lead to bearing seizure. To minimize the incidence of seizure and reduce wear, the bearing assembly ordinarily must be constructed to aggressive tolerances that drive up the cost and complexity of manufacture. In artificial heart applications, notwithstanding cost and complexity of manufacture, bearing failure can be catastrophic. Accordingly, bearing design improvements remain a constant focus for the blood pump industry.

SUMMARY

The present invention is directed to a motor rotor assembly for use in a blood pump. The motor rotor assembly may be useful in pumps configured for implantable or extracorporeal applications. Also, such pumps may take the form of rotary pumps, such as axial flow or centrifugal flow pumps. Axial flow pumps will be described herein for purposes of illustration.

The motor rotor assembly can include an inflow bearing disposed within the blood flow conduit proximal to an inflow port of the blood flow conduit, an outflow bearing disposed within the blood flow conduit proximal to an outflow port of the blood flow conduit, and a motor rotor disposed within a blood flow conduit and rotatably mounted between the inflow bearing and the outflow bearing. An inflow end of the rotor forms an inflow ball-and-cup bearing interface with the inflow bearing, and an outflow end of the rotor forms an outflow ball-and-cup bearing interface with the outflow bearing.

In accordance with an embodiment of the present invention, the outer diameter of the outflow ball-and cup bearing interface is larger than an outer diameter of the inflow ball-and-cup bearing interface. For example, the diameter of the outflow ball-and-cup bearing interface can be made at least two times larger and, in some embodiments, at least three times larger than the diameter of the inflow ball-and-cup bearing interface. Also, the diameter of the outflow ball-and-cup bearing interface can be less than or about equal to the largest diameter of the motor rotor.

Each of the ball-and-cup bearing interfaces can include a ball portion and a cup portion, the ball portion being disposed against the cup portion to form a ball-and-cup bearing interface therebetween. The resulting bearing interface may be substantially hemispherical in shape. The ball portions of each ball-and-cup bearing interfaces can be oriented to face the inflow port. For example, the ball portion of the inflow ball-and-cup bearing interface can be disposed on the inflow end of the rotor with the ball portion being oriented to face the inflow port. In this case, the inflow bearing defines a cup-like area for receipt of the ball portion of the rotor. Similarly, the ball portion of the outflow ball-and-cup bearing interface can be disposed on the outflow bearing for receipt in a cup-like portion disposed at the outflow end of the rotor.

The motor rotor assembly can also include inflow and outflow stator hubs disposed within the blood flow conduit to support inflow and outflow stator blades, respectively. The outflow stator hub, for example, can have an inflow end proximal to the motor rotor, and an outflow end proximal to the outflow port. Further, the outflow stator hub can be smaller at an end of the outflow stator hub that is more proximal to the outflow port than a diameter of the outflow stator hub that is more proximal to the motor rotor.

The outflow bearing may be secured to the outflow stator hub. In such embodiments, the ball portion of the outflow ball-and-cup bearing interface can be disposed on the inflow end of the outflow stator hub and oriented to face the inflow port. Also, the inflow bearing may be secured to the inflow stator hub, with the cup-like area of the inflow bearing being disposed at the outflow end of the inflow stator hub. Alternative orientations are conceivable, e.g., orientations in which the ball portions of both the inflow ball-and-cup bearing interface and the outflow ball-and-cup bearing interface are oriented to face the outflow port.

One or more flow stator blades can be secured to the outflow stator hub. For example, each stator blade can extend radially outward from the stator hub and toward an inner wall of the blood flow conduit. Each stator blade can have a leading edge and a trailing edge with the trailing edge being more proximal to the outflow port than the leading edge. In such an arrangement, the outflow ball-and-cup bearing interface can be disposed at a point that is more proximal to the inflow port than the leading edge of the stator blade. Alternatively, the stator blade can be extended such that the leading edge is disposed at a point that is more proximal to the inflow port than the outflow bearing interface.

A bearing assembly, in accordance with an embodiment of the present invention, can provide a number of advantages.

For example, a motor rotor assembly or blood pump incorporating aspects of the invention may be constructed from fewer parts. In particular, integration of the stator hubs and bearings can reduce the number of discrete components and assembly steps. Using fewer parts can facilitate reduced manufacturing costs and complexity, and improve pump reliability. Reducing blood pump complexity can improve pump performance and lower the risk of thrombogenesis. For example, outflow stator blades can be attached to a stator hub along their entire longitudinal length. Further, larger bearings are easier to manufacture due to reduced tolerances. Fewer parts also decrease the number of tolerances that must be monitored.

A larger bearing assembly can obviate the need for a diffuser cone required by some designs, as well as the associated close-running clearances between the diffuser cone and the stator blades. Larger bearing sizes can reduce the incidence of bearing fracture during manufacture and/or handling, due to greater structural integrity and robustness. Further, fewer parts can translate into fewer thrombosis initiation points. In summary, a motor rotor assembly or blood pump in accordance with the present invention may significantly improve the performance, reliability, and longevity of the motor rotor assembly.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference numbers and designations in the various drawings indicate like elements.

DETAILED DESCRIPTION

Figure 1:
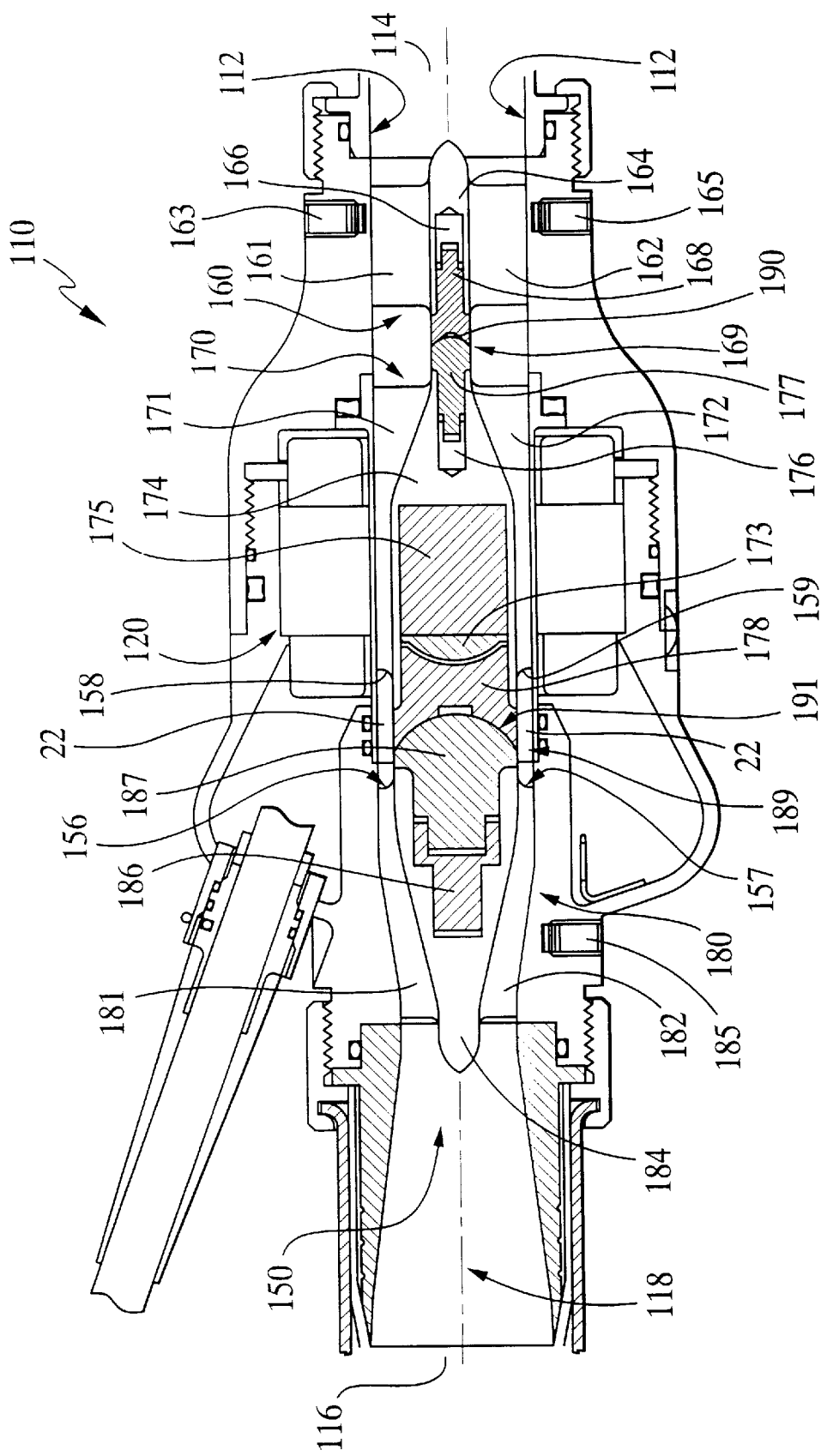
FIG. 1 is a longitudinal cross-sectional diagram depicting an implantable blood pump having an enlarged bearing design.

FIG. 1 is a longitudinal cross-sectional diagram depicting an implantable blood pump 110 incorporating aspects of the invention. As shown in FIG. 1, blood pump 110 may include an annular motor stator assembly 120 disposed about a blood flow conduit 112, and a motor rotor assembly 150 disposed within and extending axially along a longitudinal axis 118 of blood flow conduit 112. Motor rotor assembly 150 can include bearing assemblies that include an inflow bearing block 160 and an outflow bearing block 180, along with a motor rotor 170 disposed between bearing blocks 160, 180. Blood pump 110 can be configured for implantable or extracorporeal applications and can be sized accordingly. An implantable configuration will be described herein for purposes of example.

In more detail, blood enters blood pump 110 via blood flow conduit 112 through an inflow port 114 and exits an outflow port 116. Bearing block 160 can be disposed proximal to inflow port 114. Inflow stator blades 161, 162 can be located within blood flow conduit 112 between, for example, inflow port 114 and motor rotor 170. Inflow stator blades 161, 162 operate to direct blood flow, and also provide support to bearing block 160 with a minimal amount of blood flow obstruction as the blood passes through blood pump 110. Inflow stator blades 161, 162 can extend radially outward from an inflow stator hub 164 forming part of bearing block 160, and can be positioned to contact the inner wall of blood conduit 112.

FIG. 1 displays only two inflow stator blades 161, 162. However, any number of inflow stator blades, e.g., one, three, four, or five, can be arranged around inflow stator hub 164 for support. Inflow stator blades 161, 162 are typically thin and can be designed to minimize disruption of the blood flow as the blood passes through blood pump 110. Inflow stator blades 161, 162 can be formed integrally, e.g., by casting, machining, or molding, with stator hub 164. Alternatively, inflow stator blades 161, 162 can be attached to stator hub 164, e.g., by welding. Inflow stator blades 161, 162 can be fixed within blood flow conduit 112 to anchor stator hub 164, e.g., by welding, cross-pinning, set screws, or taper-lock arrangements. FIG. 1 illustrates the use of set screws 163, 165.

Blood exits blood pump 110 via blood flow conduit 112 through an outflow port 116. Outflow bearing block 180 can be disposed within blood flow conduit 112 proximal to outflow port 116. Outflow stator blades 181, 182 extend radially from an outflow stator hub 184. In addition, the outflow stator blades 181, 182 can be positioned to contact the inner wall of the blood flow conduit 112. FIG. 1 displays only two outflow stator blades 181, 182. Any number of outflow stator blades, e.g., one, two, three, four, or five, can be arranged around inflow stator hub 184 for support. Like inflow stator blades 161, 162, outflow stator blades 181, 182 can be integrally formed with outflow stator hub 184, or constitute a discrete component that is fastened to the outflow stator hub. Also, outflow stator blades 181, 182 can be fixed within blood flow conduit 112 in a manner similar to inflow stator blades 161, 162 to support outflow stator hub 184, e.g., with set screw 185. Typically, outflow stator blades 181, 182 have at least a portion of their surface curved. The curved surface of each stator blade 181, 182 serves to re-orient the flow of blood from a rotational direction to a more axial direction as the blood exits rotor assembly 150 and blood pump 110.

Still referring to FIG. 1, rotor assembly 150 includes an elongated motor rotor 170. Motor rotor 170 can be rotatably mounted between bearing block 160 and bearing block 180 on bearing assemblies 169, 189. Motor rotor 170 can be propelled by a rotating electromagnetic force generated by motor stator assembly 120. The electromagnetic force that is generated imparts a force on a magnet 175 associated with rotor hub 174, thereby actuating the motor rotor about its longitudinal axis 118. Impeller blades 171, 172 can be affixed to rotor hub 174, e.g., by welding or machining, and function to impart axial-flow energy to the blood as the motor rotor turns. In FIG. 1, only two impeller blades 171, 172 are visible. Rotor hub 174 can have any number of impeller blades, e.g., one, three, four, or five, each arranged, for example, in a spiral-like pattern. There can be a space 22 disposed between the impeller blades 171, 172 and the outflow stator blades 181, 182. The space 22 can be modified so as to minimize disruption of the blood flow through the blood pump 110.

In FIG. 1, bearing assemblies 169, 189 depict ball-and-cup bearings. The ball-and-cup bearings include at least two pieces. One piece can be a hemispherically convex "ball" portion, whereas the other piece can be a hemispherically concave "cup" portion. Both pieces are typically manufactured so that the ball portion fits into the cup portion in a reciprocal fashion, forming a substantially hemispherical bearing interface. In FIG. 1, the ball portions, i.e., bearing portions 177, 187, are oriented to face the inflow port 114. It is to be understood, however, that other orientations of bearing portions 177, 187, e.g., facing the outflow port 116 can be used.

Inflow bearing assembly 169 includes a bearing portion 168 and a bearing portion 177. Bearing portion 168 is seated in bearing seat 166, whereas bearing portion 177 is seated in bearing seat 176. Bearing seat 166 can be disposed within and bonded or suitably secured to inflow stator hub 164 using known methods. Bearing seat 176 can be disposed within rotor hub 174 in a similar fashion. Further, bearing portion 168 and bearing portion 177 can be reciprocally ground by methods known to those of skill in the art so as to produce a reciprocally matched bearing interface, as generally indicated in cross-section by the arc indicated by reference numeral 190.

Bearing assembly 189 includes a bearing portion 178 and a bearing portion 187. Bearing portion 178 can be disposed within the outflow end of rotor hub 174 and adjacent to a magnet cap 173 that functions to retain magnet 175 within the rotor hub. The magnet cap 173 can restrict the rotation of the magnet 175 and can form a hermetic enclosure for the magnet 175. Bearing portion 187 can be seated within bearing seat 186, which can be bonded to stator hub 184. Like bearing portions 168, 177, bearing portion 178 and bearing portion 187 can be reciprocally ground to produce a matched bearing interface, as generally indicated in cross-section by the arc indicated by reference numeral 191. Attachment of bearing seat 186 to stator hub 184 can be achieved in a manner similar to attachment of bearing seat 166 within stator hub 164.

Figure 2:
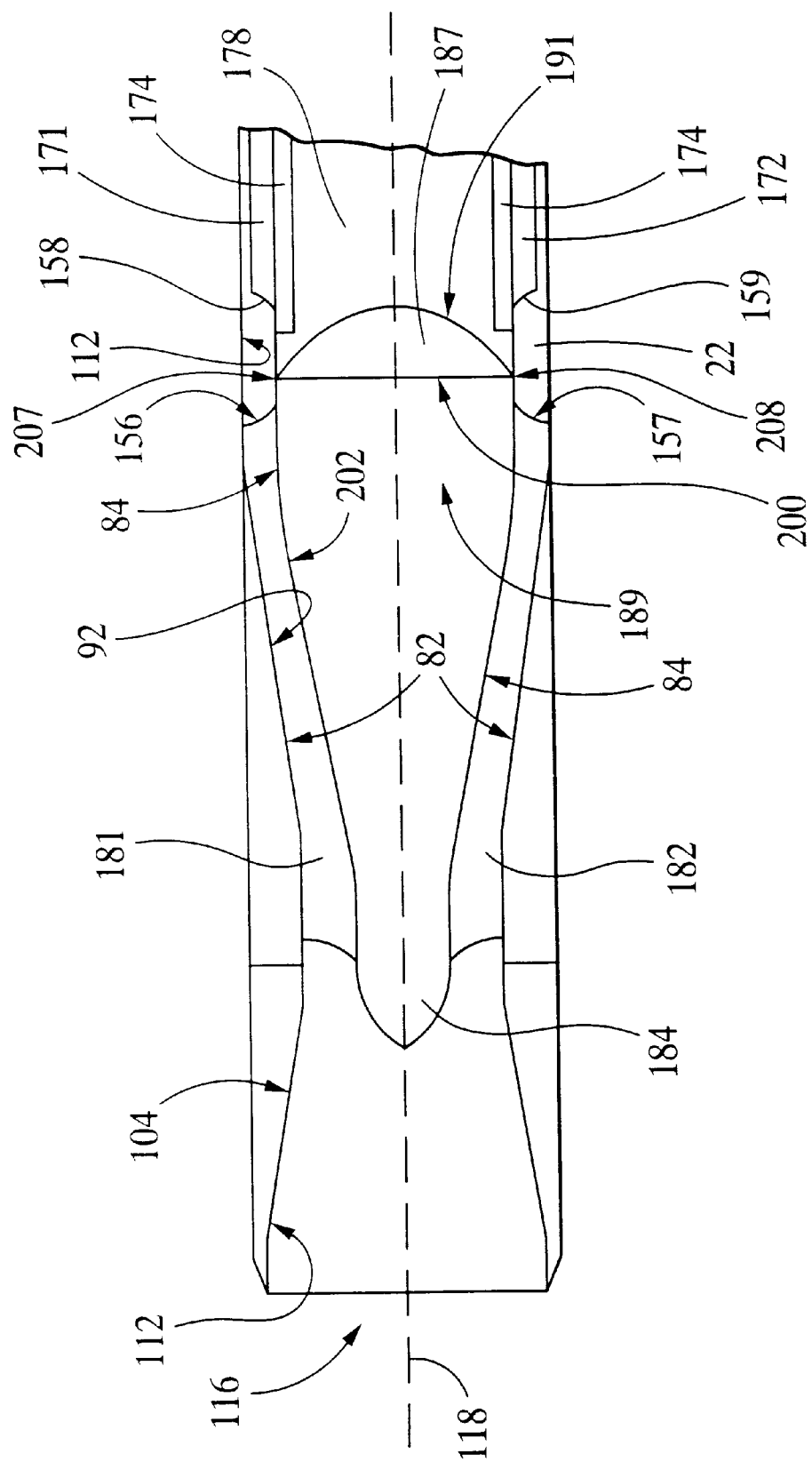
FIG. 2 is an enlarged longitudinal cross-sectional diagram conceptually depicting an enlarged bearing region as shown in FIG. 1.

FIG. 2 is a conceptual enlarged view of the outflow region of FIG. 1 illustrating bearing assembly 189. As is apparent from FIGS. 1 and 2, bearing assembly 189 has a diameter 200 that is larger than the diameter of bearing assembly 169 (not shown). It is to be understood that reference to the diameter 200 of bearing assembly 189 refers to the larger of either the diameter of bearing portion 187 or bearing portion 178 measured at the outer edge (generally indicated by reference numerals 207, 208) of the bearing interface 191. Similarly, the diameter of bearing assembly 169 refers to the larger of either the diameter of bearing portion 177 or bearing portion 168 measured at the outer edge of bearing interface 190. The size of diameter 200 can be largely dictated by the longitudinal disposition of bearing interface 191. For example, in FIG. 2, when the bearing interface 191 is disposed at a point along longitudinal axis 118 between leading edges 156, 157 of stator blades 181, 182 and trailing edges 158, 159 of impeller blades 171, 172, diameter 200 can approximate the diameter of rotor hub 174 measured at the end of the rotor hub 174 that is proximal to bearing interface 200. Accordingly, diameter 200 can be less than or about equal to a largest diameter of the motor rotor 170.

The diameter of rotor 170 can be measured without regard to the dimensions of impeller blades 171, 172. Further, the diameter 200 can approximate the diameter of the stator hub 184 measured at the end of the stator hub 184 that is proximal to bearing interface 191. Again, the diameter of stator hub 184 at the outer edge 207, 208 of bearing interface 191 would be measured without regard to stator blades 181, 182. Such an embodiment facilitates a relatively smooth transition from the motor rotor 170 to the bearing block 180 at the outer edges 207, 208 of interface 191. Placing the outer edge 207, 208 between leading edges 156, 157 and trailing edges 158, 159 can facilitate securing stator blades 181, 182 to an outer edge 84 of stator hub 184 and to an inner edge 82 of the blood flow conduit 112 along the entire longitudinal length of the stator blades 181, 182. Such positioning can be advantageous because when the outer edge 207, 208 is disposed more proximal to the outflow port than leading edges 156, 157, the stator blades 181, 182 cannot be attached to the outer edge 84 of the stator hub 184 along the entire longitudinal length of stator blades 181, 182. Instead, a portion of stator blades 181, 182 will overhang the bearing interface 191. Consequently, attachment may require more exacting manufacturing precision to ensure that the stator blades 181, 182 are suitably secured and that any spaces created in the blood flow conduit 112 do not disrupt the blood flow. Further, if the outer edge 207, 208 is disposed more proximal to the inflow port than the trailing edges 158, 159, the same manufacturing concerns that apply to stator blades 181, 182 will apply to the impeller blades 171, 172.

Compared to the diameter of a bearing interface for the inflow bearing assembly 169 (generally indicated by reference numeral 190 in FIG. 1), bearing diameter 200 can be at least about two times larger and, in some embodiments, at least about three times larger. This diameter can be realized by effectively distributing the dimensions of stator hub 184 and rotor 170 axially along blood flow conduit 112. In particular, bearing interface 191 can be disposed between leading edges 156, 157 and trailing edges 158, 159. The positioning of bearing interface 191 further upstream within blood conduit 112 allows outflow stator blades 181, 182 to have a greater effective length for more gradual redirection of blood flow. In this manner, outflow stator blades 181, 182 can be constructed to reduce shear stresses acting on the blood, and thereby minimize hemolysis. In addition, the taper desired for velocity adjustment of the blood flow can be distributed to the fixed stator hub 184 instead of the rotating rotor 170.

At the same time, stator blades 181, 182 can have lengths substantially commensurate with the length extending from the trailing edge of stator hub 184 to bearing interface 191. Consequently, leading edges 156, 157 of outflow stator blades 181, 182 need not overhang any portion of rotor 170, reducing the likelihood of bearing seizure due to accumulation of thrombus in the gap separating the rotor from the outflow stator blades. Also, the enlarged size of bearing assembly 169 can facilitate manufacturing by relaxing manufacturing and assembly tolerances. For example, with the lack of an overhang, the structure of outflow stator blades 181, 182 is less complex to machine. Precise dimensions for overhung blades, e.g., stator blades 181, 182, can be difficult to achieve because the blades can deflect under a cutting load. After fabrication, overhung blades can be susceptible to temperature variations, which can make measuring the sizes of the overhung blades difficult. Further, an enlarged bearing provides greater structural integrity and robustness to the bearing interface.

As one example, referring to FIG. 1, in a blood pump 110 sized for implantation in a human, the outer diameter 200 (see FIG. 2) of bearing interface 191 of bearing assembly 189 could be about 0.38 inches diameter and a corresponding diameter of bearing interface 190 of bearing assembly 169, measured using the methods described above, could be about 0.125 inches in diameter. In this case, bearing interface 191 would have a diameter that is approximately three times larger than the diameter of bearing interface 190. In other embodiments, the bearing 189 may be slightly larger, about one and one-half times, or about two times as large as bearing assembly 169. In other embodiments, the bearing 189 may be at least about one one-half times, or at least about two times larger than the bearing assembly 169. Typically, the largest diameter for the bearing diameter 200 will be no larger than the largest diameter of rotor hub 174, notwithstanding impeller blades 171, 172 attached to the rotor hub. Also, different diameters may result in different axial lengths for stator hub 184 and stator blades 181, 182.

Bearing 189 can be disposed at other points along the longitudinal axis 118. In embodiments having a tapering or narrowing stator hub as depicted in FIG. 2, the diameter 200 may decrease as the position of the bearing 189 becomes more proximal to the outflow port 116. For example, in FIG. 2 the diameter 200 of bearing 189 would decrease if the location of bearing 189 is such that the outer edge 207, 208 is disposed at a point along tapering portion 202. The decrease in diameter 200 would occur because, as shown in FIG. 2, the diameter 200 is largely dictated by the location of inner edge 84, which becomes more proximal to the longitudinal axis 118 at points that are proximal to the outflow port 116. Accordingly, in such an embodiment, the overall length of the stator hub 184 would decrease and the total length of the rotor 170 would increase. As an additional consequence, when the outer edge 207, 208 is positioned more proximal to the outflow port 116 than the leading edges 156, 157, the inner edge portion 84 of stator blades 181, 182 that is distal to the outer edge 207, 208 cannot be attached to the stator hub 184 unless the leading edges 156, 157 are disposed along the longitudinal axis 118 at a point that is more proximal to the outflow port than outer edge 207, 208.

As further shown in FIGS. 1 and 2, a motor rotor assembly in accordance with the invention can be used in an axial flow blood pump that features slanting or angling outflow components. For example, axial-flow blood pumps featuring slanting outflow components are disclosed in U.S. patent application Ser. No. 09/237,724, to Pieter W. C. J. le Blanc et al., filed concurrently with this application, entitled "Blood Pump with Profiled Outflow Region," and the entire content of which is incorporated herein by reference. With further reference to FIG. 2, blood flow conduit 112 can contain an angling portion 92 having an angle that extends toward longitudinal axis 118 and in a direction toward outflow port 116 such that blood flow conduit 112 constricts in that region. The constricting of blood flow conduit 112 can proceed in a direction toward outflow port 116.

As indicated above, stator hub 184 can contain a tapering portion 202 having a taper that proceeds toward longitudinal axis 118 and in a direction toward outflow port 116. In addition, blood flow conduit 112 can contain an expanding portion 104 proximal to the outflow port 116. The expanding of blood flow conduit 112 can proceed in a direction toward outflow port 116. It is noted that the net result of the constricting portion 92 and the tapering portion 202 creates a blood flow field having a cross-sectional area that increases, at least at some point, in the direction toward outflow port 116. The combined effect is more gradual reorientation of the blood flow exiting the motor rotor 170 that together with the rotor assembly 189 can function to minimize blood damage.

Figure 3:
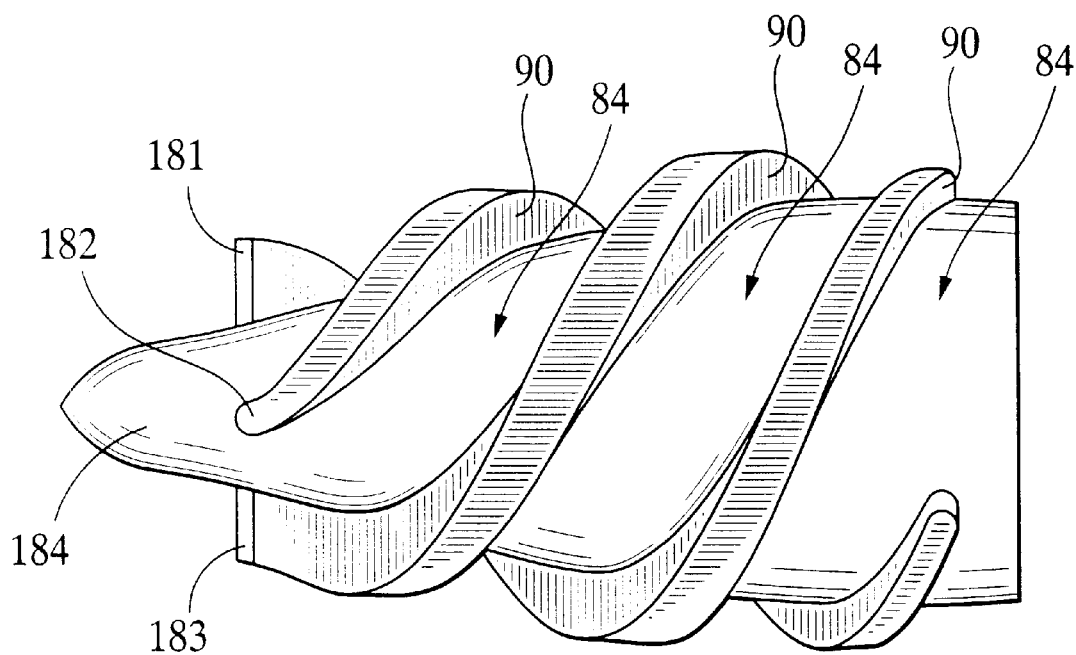
FIG. 3 is a side view diagram depicting a stator hub as depicted in FIG. 1 having three stator blades.

FIG. 3 is a side view diagram of stator hub 184 having three stator blades 181, 182, 183 each having a major surface 90 that can be curved along the entire length of the blades. Each outflow stator blade 181, 182, 183 has a major surface 90 extending from outer edge 82 (see FIG. 2) to the inner edge 84. At least a portion of this major surface can be curved. The curved major surface 90 of each stator blade can serve to re-orient the flow of blood in a more axial direction.

Methods for manufacturing ball-and-cup bearings for use in blood pumps are known. Further, blood pumps having slanting outflow components as described herein with respect to FIGS. 1–3 can be readily manufactured. Again, each blood pump component can be constructed from materials that are compatible with implantation. For example, titanium or other biocompatible metals can be used to make, without limitation, a stator hub, outflow stator blade, and an inner wall of a blood flow conduit, and other components as the blood pump 110 design necessitates.

In another embodiment, blood pump designs incorporating motor rotor assemblies having an outflow bearing that is larger than an inflow bearing can be used in both implantable and extracorporeal blood pumps that feature articulating motor stator assemblies. For example, extracorporeal blood pumps and implantable blood pumps featuring articulating stators are disclosed in U.S. patent application Ser. No. 09/237,731, to Timothy R. Maher et al., filed concurrently with this application, entitled "Articulated Motor Stator Assembly for a Pump," the entire content of which is incorporated herein by reference.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A motor rotor assembly for use in a blood pump comprising:

an inflow bearing disposed within the blood flow conduit proximal to an inflow port of the blood flow conduit;

an outflow bearing disposed within the blood flow conduit proximal to an outflow port of the blood flow conduit; and a motor rotor disposed within a blood flow conduit and rotatably mounted between the inflow bearing and the outflow bearing, an inflow end of the rotor forming an inflow ball-and-cup bearing interface with the inflow bearing, and an outflow end of the rotor forming an outflow ball-and-cup bearing interface with the outflow bearing, wherein an outer diameter of the outflow ball-and cup bearing interface is larger than an outer diameter of the inflow ball-and-cup bearing interface.

2. The motor rotor assembly of claim 1, the diameter of the outflow ball-and-cup bearing interface being at least about two times larger than the diameter of the inflow ball-and-cup bearing interface.

3. The motor rotor assembly of claim 1, the diameter of the outflow ball-and-cup bearing interface being at least about three times larger than the diameter of the inflow ball-and-cup bearing interface.

4. The motor rotor assembly of claim 1, the diameter of the outflow ball-and-cup bearing interface being less than or about equal to a largest diameter of the motor rotor.

5. The motor rotor assembly of claim 1, the motor rotor assembly being sized for use in an implantable blood pump.

6. The motor rotor assembly of claim 1, the motor rotor assembly being sized for use in an extracorporeal blood pump.

7. The motor rotor assembly of claim 1, wherein each of the ball-and-cup bearing interfaces includes a ball portion and a cup portion, the ball portion being disposed against the cup portion to form a ball-and-cup bearing interface therebetween.

8. The motor rotor assembly of claim 7, the ball portion of the inflow ball-and-cup bearing interface being disposed on the inflow end of the rotor and the ball portion being oriented to face the inflow port.

9. The motor rotor assembly of claim 7, further comprising an outflow stator hub disposed within the blood flow conduit, the outflow stator hub having an inflow end proximal to the motor rotor, and the outflow stator hub having an outflow end proximal to the outflow port.

10. The motor rotor assembly of claim 9, the ball portion of the outflow ball-and-cup bearing interface being disposed on the inflow end of the outflow stator hub and the ball portion of the outflow ball-and-cup bearing interface being oriented to face the inflow port.

11. The motor rotor assembly of claim 9, the ball portion of the inflow ball-and-cup bearing interface being disposed on the inflow end of the rotor and the ball portion being oriented to face the inflow port, and the ball portion of the outflow ball-and-cup bearing interface being disposed on the inflow end of the outflow stator hub and the ball portion being oriented to face the inflow port.

12. The motor rotor assembly of claim 9, further comprising at least one stator blade secured to the outflow stator hub, wherein the stator blade extends radially towards an inner wall of the blood flow conduit, and wherein the stator blade has a leading edge and a trailing edge, the trailing edge being more proximal to the outflow port than the leading edge, and wherein the outflow ball-and-cup bearing interface is disposed at a point that is more proximal to the inflow port than the leading edge of the stator blade.

13. The motor rotor assembly of claim 9, wherein an outer diameter of the outflow stator hub is smaller at an end of the outflow stator hub that is more proximal to the outflow port than a diameter of the outflow stator hub that is more proximal to the motor rotor.

14. The motor rotor assembly of claim 13, the outflow bearing being secured to the outflow stator hub.

15. The motor rotor assembly of claim 14, further comprising at least one stator blade secured to the outflow stator hub, the stator blade extending radially towards an inner wall of the blood flow conduit, and the stator blade having a leading edge and a trailing edge, the trailing edge being more proximal to the outflow port than the leading edge.

16. The motor rotor assembly of claim 15, the outflow ball-and-cup bearing interface being disposed at a point that is more proximal to the inflow port than the leading edge of the stator blade.

17. The motor rotor assembly of claim 16, the outflow ball-and-cup bearing interface being at least about three times larger than the diameter of the inflow ball-and-cup bearing interface.

18. The motor rotor assembly of claim 15, the leading edge being disposed at a point that is more proximal to the inflow port than the outflow ball-and-cup bearing interface.

19. An axial-flow blood pump comprising:
 a blood flow conduit having an inflow port and an outflow port;
 a motor stator;
 a motor rotor disposed within the blood flow conduit;
 an inflow bearing having an inflow ball-and-cup bearing interface disposed within the blood flow conduit proximal to an inflow port of the blood flow conduit and proximal to an inflow end of the motor rotor;
 an outflow bearing having an outflow ball-and-cup bearing interface disposed within the blood flow conduit proximal to an outflow port of the blood flow conduit and the outflow ball-and-cup bearing interface being proximal to an outflow end of the motor rotor, the motor rotor being rotatably mounted between the inflow bearing and the outflow bearing, and an outer diameter of the outflow ball-and-cup bearing interface being larger than an outer diameter of the inflow ball-and-cup bearing interface.

20. The blood pump of claim 19, the outer diameter of the outflow ball-and-cup bearing interface being at least about two times larger than the outer diameter of the inflow ball-and-cup bearing interface.

21. The blood pump of claim 19, the outer diameter of the outflow ball-and-cup bearing interface being at least about three times larger than the outer diameter of the inflow ball-and-cup bearing interface.

22. The blood pump of claim 19, the outer diameter of the outflow ball-and-cup bearing interface being larger than the outer diameter of the inflow ball-and-cup bearing interface, and the outer diameter of the outflow ball-and-cup bearing interface being smaller than a largest diameter of the motor rotor.

23. The blood pump of claim 19, the motor rotor assembly being sized for use as an implantable blood pump.

24. The blood pump of claim 19, the motor rotor assembly being sized for use in an extracorporeal blood pump.

25. The blood pump of claim 19, wherein each of the ball-and-cup bearing interfaces includes a ball portion and a cup portion, the ball portion being disposed against the cup portion to form a ball-and-cup bearing interface therebetween.

26. The blood pump of claim 25, the ball portion of the inflow ball-and-cup bearing interface being disposed on the inflow end of the rotor and the ball portion being oriented to face the inflow port.

27. The blood pump of claim 25, further comprising an outflow stator hub disposed within the blood flow conduit, the outflow stator hub having an inflow end proximal to the motor rotor, and the outflow stator hub having an outflow end proximal to the outflow port.

28. The blood pump of claim 27, the ball portion of the outflow ball-and-cup bearing interface being disposed on the inflow end of the outflow stator hub and the ball portion being oriented to face the inflow port.

29. The blood pump of claim 27, the ball portion of the inflow ball-and-cup bearing interface being disposed on the inflow end of the rotor and the ball portion being oriented to face the inflow port, and the ball portion of the outflow ball-and-cup bearing interface being disposed on the inflow end of the outflow stator hub and the ball portion being oriented to face the inflow port.

30. The blood pump of claim 27, further comprising at least one stator blade secured to the outflow stator hub, wherein the stator blade extends radially towards an inner wall of the blood flow conduit, and wherein the stator blade has a leading edge and a trailing edge, the trailing edge being more proximal to the outflow port than the leading edge, and wherein the outflow ball-and-cup bearing interface is disposed at a point that is more proximal to the inflow port than the leading edge of the stator blade.

31. The blood pump of claim 27, wherein an outer diameter of the outflow stator hub is smaller at an end of the outflow stator hub that is more proximal to the outflow port than an outer diameter of the outflow stator hub that is more proximal to the motor rotor.

32. The blood pump of claim 31, the outflow bearing being secured to the outflow stator hub.

33. The blood pump of claim 32, further comprising at least one stator blade secured to the outflow stator hub, the stator blade extending radially towards an inner wall of the blood flow conduit, and the stator blade having a leading edge and a trailing edge, the trailing edge being more proximal to the outflow port than the leading edge.

34. The blood pump of claim 33, the outflow ball-and-cup bearing interface being disposed at a point that is more proximal to the inflow port than the leading edge of the stator blade.

35. The blood pump of claim 33, the outflow ball-and-cup bearing interface being at least about three times larger than the outer diameter of the inflow ball-and-cup bearing interface.

36. The blood pump of claim 33, the leading edge disposed at a point that is more proximal to the inflow port than the outflow ball-and-cup bearing interface.

* * * * *